US009080934B2

(12) United States Patent
Nadeev et al.

(10) Patent No.: US 9,080,934 B2
(45) Date of Patent: Jul. 14, 2015

(54) METHOD FOR DETERMINING WETTABILITY OF POROUS MATERIALS

(75) Inventors: Alexander Nadeev, Moscow (RU); Dmitry Alexandrovich Korobkov, Moscow (RU); Sergey Sergeevich Safonov, Moscow (RU)

(73) Assignee: Schlumberger Technology Corporation, Sugar Land, TX (US)

( * ) Notice: Subject to any disclaimer, the term of this patent is extended or adjusted under 35 U.S.C. 154(b) by 414 days.

(21) Appl. No.: 13/553,556

(22) Filed: Jul. 19, 2012

(65) Prior Publication Data

US 2013/0019659 A1 Jan. 24, 2013

(30) Foreign Application Priority Data

Jul. 22, 2011 (RU) ................................ 2011130451

(51) Int. Cl.
*G01N 15/08* (2006.01)
*G01N 13/00* (2006.01)
G01N 7/04 (2006.01)
G01N 13/02 (2006.01)

(52) U.S. Cl.
CPC ............... *G01N 15/08* (2013.01); *G01N 13/00* (2013.01); *G01N 7/04* (2013.01); *G01N 2013/0208* (2013.01)

(58) Field of Classification Search
CPC ......... G01N 15/08; G01N 13/00; G01N 7/04; G01N 2013/0208
USPC ............................................................ 73/38
See application file for complete search history.

(56) References Cited

U.S. PATENT DOCUMENTS

| 5,069,065 | A | * | 12/1991 | Sprunt et al. | 73/152.09 |
| 5,425,265 | A | * | 6/1995 | Jaisinghani | 73/38 |
| 7,776,602 | B2 | * | 8/2010 | Reznek et al. | 436/2 |
| 7,776,604 | B2 | * | 8/2010 | Brown et al. | 436/2 |

(Continued)

FOREIGN PATENT DOCUMENTS

| RU | 2216723 C1 * | 11/2003 | ............. G01N 13/02 |
| SU | 602827 A1 | 4/1978 | |

(Continued)

OTHER PUBLICATIONS

Amott, E., "Observations Relating to the Wettability of Porous Rock", Petroleum Transactions, AIME, vol. 216, 1959, pp. 156-162.

(Continued)

*Primary Examiner* — Hezron E Williams
*Assistant Examiner* — Tarun Sinha

(57) ABSTRACT

Method for determining wettability of porous materials comprises placing a sample of a porous material into a cell of a calorimeter and contacting the sample with a wetting fluid. A heat flow into the cell is continuously measured. Based on results of the measurement and taking into account a thermal effect of the fluid compression, a first wetting contact angle of pores filled with the wetting fluid is calculated. Then, a pressure in the cell containing the sample is increased starting from an initial value until pores of the sample are completely filled with the fluid. Then, the pressure is reduced to the initial value while continuously measuring of a heat flow into the cell. The method enables calculation of a second wetting contact angle for pores completely filled with the fluid and of a third wetting contact angle for pores free from the fluid.

13 Claims, 2 Drawing Sheets

(56) References Cited

U.S. PATENT DOCUMENTS

2011/0167897 A1* 7/2011 Huang et al. .................. 73/38
2011/0313712 A1* 12/2011 Nikolyn et al. ............. 702/136

FOREIGN PATENT DOCUMENTS

SU        1516887 A1   10/1989
UA           5494 A    12/1994

OTHER PUBLICATIONS

Anderson, William, "Wettability Literature Survey—Part 2: Wettability Measurement", Journal of Petroleum Technology, vol. 38 (11), Nov. 1986, pp. 1246-1262.

Denoyel, et al., "Thermodynamics of wetting: information brought by microcalorimetry", Journal of Petroleum Science and Engineering, vol. 45, Dec. 15, 2004, pp. 203-212.

Gusev, Vladimir Y., "On thermodynamics of permanent hysteresis in capillary lyophobic systems and interface characterization", Langmuir, vol. 10 (1), 1994, pp. 235-240.

Rao, et al., "A New Technique for Reservoir Wettability Characterization", Journal of Canadian Petroleum Technology, vol. 35 (1), 1996, pp. 31-39.

Rao, D.N., "Measurements of Dynamic Contact Angles in Solid-Liquid-Liquid Systems at Elevated Pressures and Temperatures", Colloids and Surfaces A: Physicochemical and Engineering Aspects, vol. 206, Jul. 9, 2002, pp. 203-216.

Trantham, et al., "Determination of oil Saturation After Waterflooding in an Oil-Wet Reservoir—The North Burbank Unit, Tract 97 Project", Journal of Petroleum Technology, vol. 29(5), 1977, pp. 491-500.

"Plastics—Differential scanning calorimetry (DSC)—Part 1: General principles", ISO 11357-1, Apr. 15, 1997, 14 pages.

* cited by examiner

US 9,080,934 B2

METHOD FOR DETERMINING WETTABILITY OF POROUS MATERIALS

CROSS-REFERENCE TO RELATED APPLICATION

This application claims priority to Russian Patent Application Serial No. RU 2011130451 filed Jul. 22, 2011, which is incorporated herein by reference in its entirety.

FIELD OF THE DISCLOSURE

The disclosure is related to investigation of surface properties, particularly, to determination of wettability of porous materials. This disclosure may be used in different areas of industry, particularly, in the oil and gas industry, the chemical industry, the paint-and-coating industry, and the food industry.

BACKGROUND OF THE DISCLOSURE

Wettability is an important phenomenon greatly impacting specifics of fluid distribution and propagation in a porous media. Thus, being a key parameter for characterizing oil formation and simulation, wettability greatly affects rock filtration properties, like relative permeability and displacement coefficient.

A wetting degree is characterized by a wetting angle. A wetting angle (or a contact wetting angle) is an angle made up by planes tangent to interface surfaces limiting a wetting fluid. A vertex of the angle lies on a boundary of three-phases.

A measurement of a contact wetting angle value is one of the most common methods of wettability measurement. Contact wetting angle is determined geometrically as an angle on a boundary of three-phases—a fluid, a gas, a solid body. The contact angle is very important for understanding material surface properties—adhesion, wettability and free energy of the system in general.

Two different approaches are commonly used to measure a contact wetting angle: an optical measurement and a force measurement of surface tension (tensiometry). Optical tensiometry includes observation of a sessile drop of a test liquid on a surface of a solid material. In force tensiometry, forces of interaction between a solid body and a test liquid are measured. Most known methods for a contact angle measurement are as follows: a sessile drop method, a capillary rise method, a tilted plate method, and an immersion plate method (cf., D. N. Rao, M. G. Girard, "A new technique for reservoir wettability characterization," J. Can. Pet. Technol., 35, 31-39 (1996), or D. N. Rao, "Measurements of dynamic contact angles in solid-liquid-liquid systems at elevated pressures and temperatures," Colloids Surf, 206, 203-216 (2002)).

However, these methods do not take into account roughness and heterogeneity of a surface and potential complex geology of a pore structure. On a smooth surface, a contact wetting angle is fixed, while on a sample surface with sharp edges, the contact wetting angles are different. Also, a contact angle is measured on a single mineral, whereas a core contains numerous minerals with impurities. Finally, organic compounds absorbed on a sample surface strongly effect wetting properties.

The known Amott method (E. Amott, "Observations Relating to the Wettability of Porous Media," Trans, AIME, 216, 156-162, 1959) combined imbibitions and forced displacement to measure an average wettability of a rock sample. The Amott method is based on the fact that a wetting fluid can spontaneously imbibe into a core simultaneously displacing a non-wetting fluid. The ratio of a spontaneous imbibition to a forced imbibition is used to reduce the influence of other factors, such as viscosity and initial rock saturation. Other scientists use modifications of the Amott method: Amott-Harvey method and USBM (cf., J. C. Trantham, R. L. Clampitt, "Determination of Oil Saturation After Waterflooding in an Oil-Wet Reservoir—The North Burbank Unit, Tract 97 Project," JPT, 491-500 (1977).

A disadvantage of the Amott method and its modifications is that the methods have a big error when applied to samples with neutral wettability or when applied to samples with small sizes (less than 1 inch).

A method for determining wettability based on calorimetric measurements has been actively developed. Calorimeters have been used for a long time to study interaction between fluids and surfaces. calorimetry helps to determine thermodynamic state functions, such as internal energy or enthalpy related to a wetting process (cf., R. Denoyel, I. Beurroies, B. Lefevre, "Thermodynamics of wetting: information brought by microcalorimetry," J. of Petr. Sci. and Eng., 45, 203-2126 2004).

An advantage of calorimetric methods is the possibility of conducting experiments in which initial and final states of a system are well determined, which is not always possible if other methods, like standard methods for contact angle measurement, are applied.

The disclosed method is directed to the study of wettability of porous samples and to determining with high accuracy a contact wettability angle for pores having different diameters.

SUMMARY OF THE DISCLOSURE

A sample of a porous material is placed into a cell of a differential scanning calorimeter and a contact of the sample with a wetting fluid is provided. A heat flow into the cell is continuously measured. Based on the results of the heat flow measurement and taking into account a thermal effect of the wetting fluid compression, a first contact wetting angle of pores partially filled with the wetting fluid due to spontaneous impregnation of a porous space of the sample at a constant pressure is calculated.

A pressure within the cell containing the sample is increased from an initial value until all pores of the sample are filled with the wetting fluid. Simultaneously, a heat flow into the cell is measured. Based on results of the heat flow measurement and taking into account a thermal effect of the wetting fluid compression, a second contact wetting angle of pores completely filled with the wetting fluid under pressure is calculated.

Then, the pressure in the cell with the sample is reduced to the initial value and a heat flow into the cell is continuously measured. Based on results of the heat flow measurement and taking into account a thermal effect of the wetting fluid compression effect, a third contact angle of pores free of the wetting fluid is calculated.

According to one embodiment of the method for determining wettability of porous materials, the wetting fluid is preliminary placed into the cell without contact between the sample and the wetting fluid. The cell containing the sample and the wetting fluid are kept at a temperature at which the wetting fluid does not undergo any phase transformations until stabilization of the heat flow, after that, a contact between the sample and the wetting fluid is provided.

It is preferable to keep the cell with the sample impregnated with the wetting fluid until stabilization of the heat flow.

Cycles of increasing and reducing the pressure in the cell can be repeated until changes of thermal effect curves during the pressure increasing and reducing have been stopped.

According to one embodiment of the method for determining wettability of porous materials, the pressure increasing and reducing is made step-by-step. At each step the cell is kept until stabilization of the heat flow and the heat flow is measured.

The thermal effect of the wetting fluid compression may be taken into account using a prior basic experiment in which the wetting fluid is supplied to the cell without a sample. The pressure in the cell is increased until a pore space of the sample in question has been filled with the fluid. The pressure in the cell is reduced to the initial value and a heat flow into the cell is measured continuously.

The sample may be dried and in some cases purified.

A core can be used as the sample of the porous material, and in this case oil, water or salt solution can be used as the wetting fluid.

DETAILED DESCRIPTION

Figure 1:
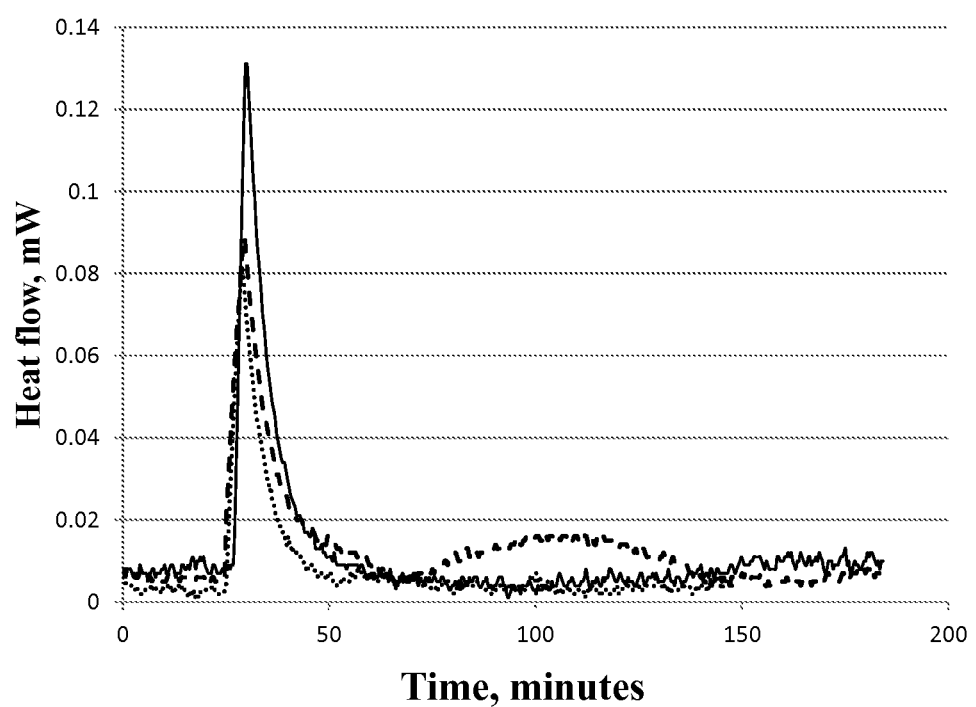
FIG. 1 shows a heat flow as a function of time at a pressure of 10 bar.

A wetting contact angle is determined by Young's equation:

$$\gamma_{sv} = \gamma_{sl} + \gamma_{lv} \cos \theta, \quad (1)$$

$\theta$—a wetting contact angle, $\gamma_{sv}$—solid/vapor interfacial free energy, $\gamma_{sl}$—solid/liquid interfacial free energy, $\gamma_{lv}$—liquid/vapor interfacial free energy.

A process of liquid intrusion/extrusion into a porous medium when a surface contacts a fluid is started at a controlled relative pressure. A free energy variation $\Delta F$ (per unit of area) can be described through a change of system internal energy $\Delta U$ using the following equations (2, 3):

$$\Delta U = \Delta F - T \frac{\partial \Delta F}{\partial T} \quad (2)$$

$$\Delta F = \gamma_{sl} - \gamma_{sv} \quad (3)$$

Using Young's equation (1) and the free energy variation it is possible to express a relationship with the wetting contact angle:

$$\Delta U = -\gamma_{lv} \cos\theta + T \frac{\partial \gamma_{lv} \cos\theta}{\partial T} = \left(-\gamma_{lv} + T \frac{\partial \gamma_{lv}}{\partial T}\right)\cos\theta + T \frac{\gamma_{lv} \partial \cos\theta}{\partial T} \quad (4)$$

Equation (4) may be approximated into equation (5) if the contact angle does not depend on the temperature.

$$\cos\theta = \frac{-\Delta U}{\left(\gamma_{lv} - T \frac{\partial \gamma_{lv}}{\partial T}\right)} \quad (5)$$

The size of pores into which the liquid is intruded may be evaluated using a Laplace formula ($p_c$—capillary pressure, r—pore radius):

$$p_c = \frac{2\gamma_{lv} \cos\theta}{r} \quad (6)$$

The disclosed method of wettability determination is based on a heat flow measurement in case of intrusion of a wetting fluid (water, solutions or oil) into a porous structure of a sample, e.g., a core (sandstone, carbonate, limestone etc.). This method may be applied for wettability determination in case of displacement of one fluid with another.

To avoid the influence of factors related to incomplete saturation of the sample with the formation fluid and/or saturation with drilling mud, the sample should be pre-treated before starting the experiment. In most cases, a sample porous space should be purified (the sample should be extracted and dried). If it is possible to collect a core preserving all rock characteristics, including wettability, a sample should only be dried.

A sample and a wetting fluid in relation to which wettability is determined (oil, water, salt solution) is placed into a cell of a differential scanning calorimeter, for example, BT2.15 (SETARAM, France, http://www.setaram.ru/BT-2.15-ru-.htm.) so as to eliminate a contact between them before the experiment starts. The cell may be filled with the fluid during the experiment if the sample, the cell and the wetting fluid temperatures are equal.

To reduce an error resulting from an additional heat flow during stabilization of a system (the cell—the sample—the fluid), the cell with the sample and the wetting fluid are kept at a preset temperature (at which the wetting fluid does not experience phase transformations) until a stabilization of heat flow (hereinafter the term "stabilization of heat flow" shall be understood as settling of a permanent thermal mode in which no heat absorption or extraction in the cell occurs and which is characterized by zero or basic heat flow). All the subsequent measurements shall be held at the permanent temperature.

The fluid-to-sample contact is provided which results in the wetting fluid contact with the sample by means of, for example, mixing cells with membrane (http://www.setaram.ru/index-ru); a heat flow into the cell is continuously measured. Pressure in the cell is equal to atmospheric pressure. The cell is kept until stabilization of heat flow. At this stage of the experiment, a thermal effect of spontaneous impregnation of a porous space of the sample at the constant pressure is determined. The integrated heat flow corresponds to a change of an internal energy of the system due to wetting of a portion of the porous space. To calculate a first contact wetting angle equations (4) and (5) may be used.

Knowing a volume of the cell, a volume of the sample, and its porosity, a volume of the porous space corresponding to lyophilic pores may be determined. Using formula (6) it is possible to evaluate which part of the lyophobic pores that come to the sample surface will be filled in case of spontaneous impregnation.

Then, pressure in the cell with the sample (overpressure relative to the atmospheric pressure) is increased at least once until all pores of the sample are filled with the wetting fluid. The pressure may be increased step-by-step or continuously; step-by-step increasing ensures a higher measurement quality and high accuracy of wettability determination. In the case of a step-by-step procedure, the pressure in the cell with the sample (overpressure relative to the atmospheric pressure) is increased to a first pressure (for example, 1 bar) and kept for the time sufficient to stabilize the heat flow. Then the pressure in the cell is increased step-by-step to the $n^{th}$ pressure (e.g., 2, 4, 10, 20, 40, 80, 150, 300 bar). Upon reaching the upper pressure all sample pores must be filled with the wetting fluid, the value may be evaluated using formula (6). The number of pressure steps depends on the sample, e.g., for microporous rocks a larger number of steps must be done in high pressure area. The cell containing the sample is kept at each step for a time sufficient to stabilize the heat flow. The volume of the wetting fluid injected into the cell with the sample is measured at each pressure step. At this stage, a volume and a wetting energy of pores with a size corresponding to the fluid filling at this pressure is determined. This value may be assessed using equation (6) and the pore volume is equal to the volume of the fluid injected at this stage except for the hydraulic system spurious volumes. For the wetting energy calculation, it is possible to eliminate a thermal effect of the wetting fluid compression. Based on results of the heat flow measurement at each pressure step, using equations (4) or (5), a second contact wetting angle of the fluid-filled pores is evaluated. Sample pores which were not filled during spontaneous injection are filled during the wetting fluid intrusion.

Then, the pressure of the wetting fluid in the cell is gradually reduced (similarly to the increase thereof, but in reverse order) to the first pressure (1 bar). At this stage a thermal effect of the fluid compression and wetting is recorded. Based on results of the heat flow measurement using equations (4) or (5), a third wetting contact angle of oleophobic pores free from the fluid is evaluated. Volumes of the fluid going out of the pore volume due to the effect of capillary forces may also be measured.

Figure 2:
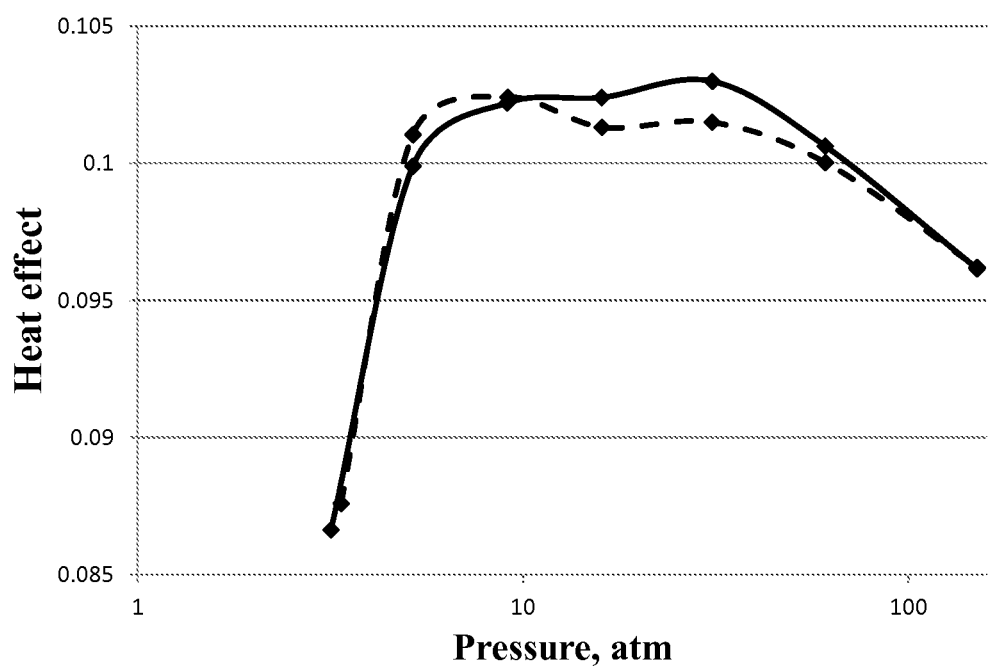
FIG. 2 shows dependence of a thermal effect normalized to pressure difference at different wetting fluid pressure values.

Cycles of increasing and reducing pressure can be repeated until the thermal effect curves stop changing. Increasing the number of the cycles improves the accuracy of the determination of wettability of a porous media. The experiment results, taking into account a thermal effect of the wetting fluid compression, are shown in FIG. 2, where a solid curve is a pressure increase and a dashed curve is a pressure reduction. The curves are given in absolute values of the integral heat flow for each pressure value (during the pressure increase an exothermic effect of the fluid compression is observed whereas in case of the pressure reduction the effect is endothermic. If there is no wettability, these effects are different in sign but equal in value). To eliminate the thermal effect of the wetting fluid compression, table data of the known fluids may be used or a basic experiment may be held—pressure increase in the cell with the fluid but without the sample. A difference between absolute values of the integrated heat flow at a given pressure resulting from the pressure increasing or reducing is a wetting heat, i.e., a change of an internal energy, this value is substituted to equation (4) or (5) to calculate the contact angle.

In one example, a wetting thermal effect has been identified during the intrusion of a salt solution into a sandstone. The main narrow peak is related to the process of a porous media compressing by fluid while pressure is increasing. The thermal by-effect corresponds to the emergence of a heat flow wide peak after the pressure stabilization, this by-effect is due to the fluid intrusion into the pore space (FIG. 1). In FIG. 1, a solid curve corresponds to a basic experiment—pressure increase in a cell without a sample. A dashed line corresponds to an experiment with a primary intrusion of a fluid into the sample (a dry sample). A dotted line is the repeated fluid intrusion into the sample. The integral thermal effect from the fluid intrusion into the sample is due to the change of the system internal energy and may be used to calculate the wettability, whereas the measured volume of the intruded fluid can be used for the determination of the pore volume at different pressure values.

This method enables calculation of a wetting contact angle for pores with different diameter, i.e., as per Laplace formula (6), the fluid pressure determines the volume of the pores being filled.

What is claimed is:

1. A method for determining wettability of porous materials comprising:
    placing a sample of a porous material into a calorimeter cell,
    contacting the sample with a wetting fluid and continuously measuring a heat flow into the cell,
    calculating a first contact wetting angle of pores partially filled with the wetting fluid due to spontaneous impregnation of a porous space of the sample at a constant pressure based on results of the heat flow measurement and taking into account a thermal effect of wetting fluid compression,
    at least once, increasing a pressure in the cell with the sample starting from an initial value to a value at which all pores of the sample are filled with the wetting fluid and continuously measuring a heat flow into the cell,
    calculating a second contact wetting angle of the pores filled with the fluid under pressure based on results of the heat flow measurement and taking into account a thermal effect of the wetting fluid compression,
    reducing the pressure in the cell with the sample to the initial value and continuously measuring a heat flow into the cell, and
    calculating a third contact wetting angle for pores free from the wetting fluid based on results of the heat flow measurement and taking into account a thermal effect of the wetting fluid compression.

2. The method of claim 1, wherein the wetting fluid is preliminarily placed into the cell containing the sample without contact between the sample and the wetting fluid and the cell containing the sample and the wetting fluid is kept held at a preset temperature, at which the fluid does not undergo phase transformations, until stabilization of heat flow.

3. The method of claim 1, wherein the cell containing the sample impregnated with the wetting fluid is held at a preset temperature until stabilization of the heat flow.

4. The method of claim 1, wherein cycles of increasing/reducing pressure in the cell are repeated until changes of curves of a thermal effect resulting from the pressure increasing/reducing have stopped.

5. The method of claim 1, wherein the pressure in the cell containing the sample is increased step-by-step and, at each step, the cell with the sample is held at a preset temperature until stabilization of the heat flow.

6. The method of claim 1, wherein the pressure in the cell with the sample is reduced step-by-step and, at each step, the cell with the sample is kept held at a preset temperature until stabilization of the heat flow.

7. The method of claim 1, wherein the wetting fluid is first injected into the cell without the sample, the pressure in the cell is increased starting from the initial value to the value at which the entire pore space of the sample has been filled, and then the pressure in the cell is reduced to the initial value while continuously measuring of a heat flow into the cell.

8. The method of claim 1, wherein the sample of the porous material is dried before placement into the calorimeter cell.

9. The method of claim 8, wherein the sample of the porous material is purified before placement into the calorimeter cell.

10. The method of claim 1, wherein a core is used as the sample of the porous material.

11. The method of claim 10, wherein the wetting fluid is oil.

12. The method of claim 10, wherein the wetting fluid is water.

13. The method of claim 10, wherein the wetting fluid is a salt solution.

* * * * *